United States Patent
Beauchamp et al.

(10) Patent No.: US 8,835,417 B2
(45) Date of Patent: Sep. 16, 2014

(54) CRYSTALLINE HYDROCHLORIDE SALT OF (1-(4-FLUOROPHENYL)-1H-INDOL-5-YL)-(3-(4-(THIAZOLE-2-CARBONYL)PIPERAZIN-1-YL)AZETIDIN-1-YL)METHANONE

(71) Applicant: Janssen Pharmaceutica NV, New Brunswick, NJ (US)

(72) Inventors: Derek A. Beauchamp, Schwenksville, PA (US); Kenneth M. Wells, Doylestown, PA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 13/628,331

(22) Filed: Sep. 27, 2012

(65) Prior Publication Data

US 2013/0085279 A1  Apr. 4, 2013

Related U.S. Application Data

(60) Provisional application No. 61/541,281, filed on Sep. 30, 2011.

(51) Int. Cl.
*A61K 31/496* (2006.01)
*C07D 417/14* (2006.01)

(52) U.S. Cl.
CPC .................... *C07D 417/14* (2013.01)

USPC ..................................... 514/210.18; 544/369

(58) Field of Classification Search
None
See application file for complete search history.

(56) References Cited

U.S. PATENT DOCUMENTS 3,609,152 A * 9/1971 Hess et al. ............... 540/600
4,337,341 A * 6/1982 Zimmerman ............. 546/112
2010/0324011 A1* 12/2010 Bian et al. ............... 514/210.18

FOREIGN PATENT DOCUMENTS

WO  WO 2010/124108  10/2010

OTHER PUBLICATIONS

Berge et al. J. of Pharmaceutical Sciences, vol. 66 p. 1-19 (1977).*
International Search Report for Application No. PCT/US2012/057461 mailed Dec. 4, 2012.

* cited by examiner

*Primary Examiner* — Emily Bernhardt
(74) *Attorney, Agent, or Firm* — Thomas J. Dodd

(57) ABSTRACT

The present invention relates to a crystalline hydrochloride salt of (1-(4-fluorophenyl)-1H-indol-5-yl)(3-(4-(thiazole-2-carbonyl)piperazin-1-yl)azetidin-1-yl)methanone, methods of making said salt, pharmaceutical compositions containing said salt, and the use of said salt in the treatment of pain and diseases that cause such pain, and metabolic disorders such as, obesity, hyperphagia, and diabetes.

3 Claims, 3 Drawing Sheets

Powder X-Ray Diffraction Spectrum for the Crystalline Form of the Hydrochloride salt of Cpd 1

CRYSTALLINE HYDROCHLORIDE SALT OF (1-(4-FLUOROPHENYL)-1H-INDOL-5-YL)-(3-(4-(THIAZOLE-2-CARBONYL)PIPERAZIN-1-YL)AZETIDIN-1-YL)METHANONE

CROSS-REFERENCE TO RELATED APPLICATIONS

This application claims priority to U.S. provisional patent application No. 61/541,281, filed Sep. 30, 2011, which is hereby incorporated by reference in its entirety.

STATEMENT REGARDING FEDERALLY SPONSORED RESEARCH OR DEVELOPMENT

The research and development of the invention described below was not federally sponsored.

FIELD OF THE INVENTION

The present invention relates to a crystalline hydrochloride salt of (1-(4-fluorophenyl)-1H-indol-5-yl)(3-(4-(thiazole-2-carbonyl)piperazin-1-yl)azetidin-1-yl)methanone, pharmaceutical compositions containing said salt, and the use of said salt in the treatment of pain and diseases that lead to such pain, and metabolic disorders such as, obesity, hyperphagia, and diabetes. The present invention is further directed to a process for the preparation of said crystalline hydrochloride salt.

SUMMARY OF THE INVENTION

The present invention relates to a crystalline form of the hydrochloride salt of (1-(4-fluorophenyl)-1H-indol-5-yl)(3-(4-(thiazole-2-carbonyl)piperazin-1-yl)azetidin-1-yl)methanone (1).

Cpd 1

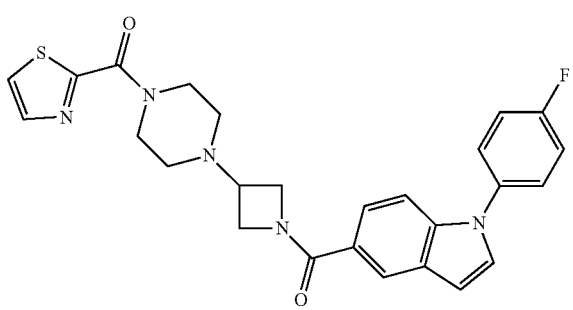

The invention also provides methods for making the hydrochloride salt of (1-(4-fluorophenyl)-1H-indol-5-yl)(3-(4-(thiazole-2-carbonyl)piperazin-1-yl)azetidin-1-yl)methanone. The invention further provides methods for making the hydrochloride salt of (1-(4-fluorophenyl)-1H-indol-5-yl)(3-(4-(thiazole-2-carbonyl)piperazin-1-yl)azetidin-1-yl)methanone in a crystalline form, as described in more detail hereinafter. Pharmaceutical compositions and methods of the invention are useful in the treatment or prevention of pain and diseases that lead to such pain, and a variety of metabolic diseases such as, obesity, hyperphagia, and diabetes.

DETAILED DESCRIPTION OF THE INVENTION

Figure 1:
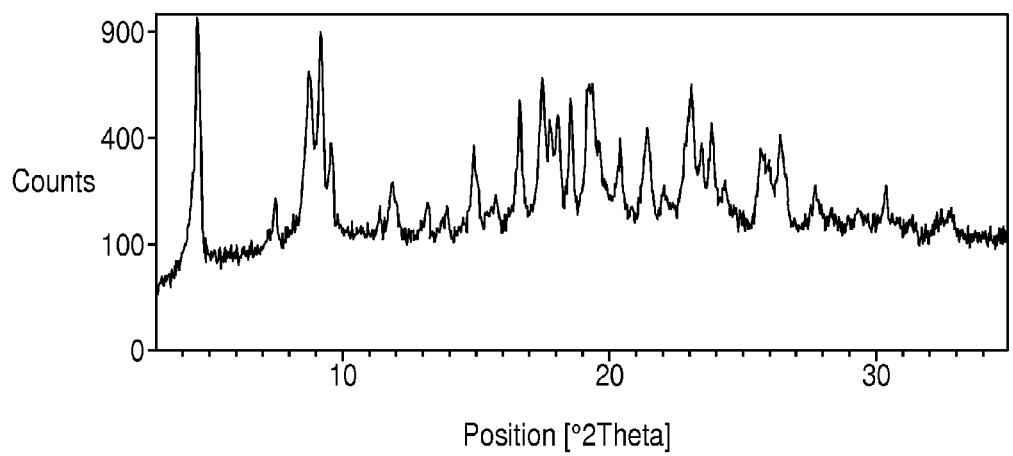
FIG. 1 illustrates a representative powder X-ray diffraction (pXRD) spectrum for the crystalline hydrochloride salt of compound 1.

The present invention is directed to a crystalline hydrochloride salt of (1-(4-fluorophenyl)-1H-indol-5-yl)(3-(4-(thiazole-2-carbonyl)piperazin-1-yl)azetidin-1-yl)methanone (Cpd 1)

Cpd 1

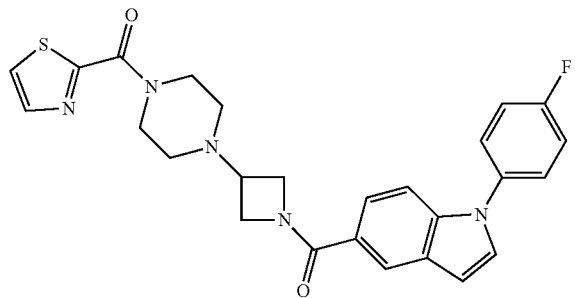

useful for the treatment or prevention of pain and diseases that lead to such pain, and a variety of metabolic diseases such as, obesity, hyperphagia, and diabetes.

The term "isolated form" as used herein, unless otherwise noted, means that the compound is present in a form that is separate from any solid mixture with another compound(s), solvent system or biological environment. In an embodiment, the present invention is directed to a hydrochloride salt of compound 1, preferably a crystalline hydrochloride salt of compound 1, wherein the salt is present and/or prepared as an isolated form.

The term "substantially pure form" as used herein, unless otherwise noted, means that the mole percent of impurities in the isolated compound is less than about 5 mole percent, preferably less than about 2 mole percent, more preferably, less than about 0.5 mole percent, most preferably, less than about 0.1 mole percent. In an embodiment, the present invention is directed to a hydrochloride salt of compound 1, preferably a crystalline hydrochloride salt of compound 1, wherein the salt is present and/or prepared as a substantially pure form.

The terms "treating", "treatment" and the like, as used herein, unless otherwise noted, includes the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, or disorder.

The term "prevention" as used herein, unless otherwise noted, includes (a) reduction in the frequency of one or more symptoms; (b) reduction in the severity of one or more symptoms; (c) the delay or avoidance of the development of additional symptoms; and/or (d) delay or avoidance of the development of the disorder or condition.

One skilled in the art will recognize that wherein the present invention is directed to methods of prevention, a subject in need of thereof (i.e., a subject in need of prevention)

includes any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (comorbid) disorders or conditions, genetic testing, and the like.

The term "subject" as used herein, unless otherwise noted, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, unless otherwise noted, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

The term "composition" as used herein, unless otherwise noted, means a product including the specified ingredients in the specified amounts, as well as any product that results, directly or indirectly, from combinations of the specified ingredients in the specified amounts.

To provide a more concise description, some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any range therein. Pharmaceutical dosage forms of the crystalline hydrochloride salt of (1-(4-fluorophenyl)-1H-indol-5-yl)(3-(4-(thiazole-2-carbonyl)piperazin-1-yl)azetidin-1-yl)methanone can be administered in several ways including, but not limited to, oral administration. Oral pharmaceutical compositions and dosage forms are exemplary dosage forms. Optionally, the oral dosage form is a solid dosage form, such as a tablet, a caplet, a hard gelatin capsule, a starch capsule, a hydroxypropyl methylcellulose (HPMC) capsule, or a soft elastic gelatin capsule. Liquid dosage forms may also be provided by the present invention, including such non-limiting examples as a suspension, a solution, syrup, or an emulsion. In another embodiment, the present invention includes the preparation of a medicament comprising a crystalline hydrochloride salt of (1-(4-fluorophenyl)-1H-indol-5-yl)(3-(4-(thiazole-2-carbonyl)piperazin-1-yl)azetidin-1-yl)methanone.

Like the amounts and types of excipients, the amounts and specific type of active ingredient in a dosage form may differ depending on factors such as, but not limited to, the route by which it is to be administered to mammals. However, typical dosage forms of the invention comprise a crystalline hydrochloride salt of (1-(4-fluorophenyl)-1H-indol-5-yl)(3-(4-(thiazole-2-carbonyl)piperazin-1-yl)azetidin-1-yl)methanone, in an amount of from about 0.10 mg to about 1.00 g, from about 0.2 mg to about 500.0 mg, or from about 1.0 mg to about 250.0 mg. Non-limiting examples include 0.2 mg, 0.50 mg, 0.75 mg, 1.0 mg, 1.2 mg, 1.5 mg, 2.0 mg, 3.0 mg, 5.0 mg, 7.0 mg, 10.0 mg, 25.0 mg, 50.0 mg, 100.0 mg, 250.0 mg, and 500.0 mg dosages. The dosages, however, may be varied depending upon the requirement of the patients, the severity of the condition being treated and the compound being employed. The use of either daily administration or post-periodic dosing may be employed.

The crystalline hydrochloride salt of (1-(4-fluorophenyl)-1H-indol-5-yl)(3-(4-(thiazole-2-carbonyl)piperazin-1-yl)azetidin-1-yl)methanone of the present invention may also be used to prepare pharmaceutical dosage forms other than the oral dosage forms described above, such as topical dosage forms, parenteral dosage forms, transdermal dosage forms, and mucosal dosage forms. For example, such forms include creams, lotions, solutions, suspensions, emulsions, ointments, powders, patches, suppositories, and the like.

Abbreviations used in the instant specification, particularly the schemes and examples, are as follows:

DCC N,N'-dicyclohexyl-carbodiimide

DCM dichloromethane

DMF N,N-dimethylformamide

DMSO dimethylsulfoxide

EDC N-(3-dimethylaminopropyl)-N'-ethylcarbodiimide hydrochloride

ESI electrospray ionization

EtOAc ethyl acetate

EtOH ethanol

HATU O-(1H-7-azabenzotriazol-1-yl)-1,1,3,3-tetramethyluronium hexafluorophosphate HOBt hydroxybenzotriazole MeCN acetonitrile MeOH methanol MHz megahertz min minutes MS mass spectrometry Ms mesyl or methanesulfonyl NMR nuclear magnetic resonance TEA/Et$_3$N triethylamine TFA trifluoroacetic acid THF tetrahydrofuran TMS tetramethylsilane

EXAMPLES

Preparation of the Hydrochloride Salt of (1-(4-Fluorophenyl)-1H-indol-5-yl)(3-(4-(thiazole-2-carbonyl)piperazin-1-yl)azetidin-1-yl)methanone

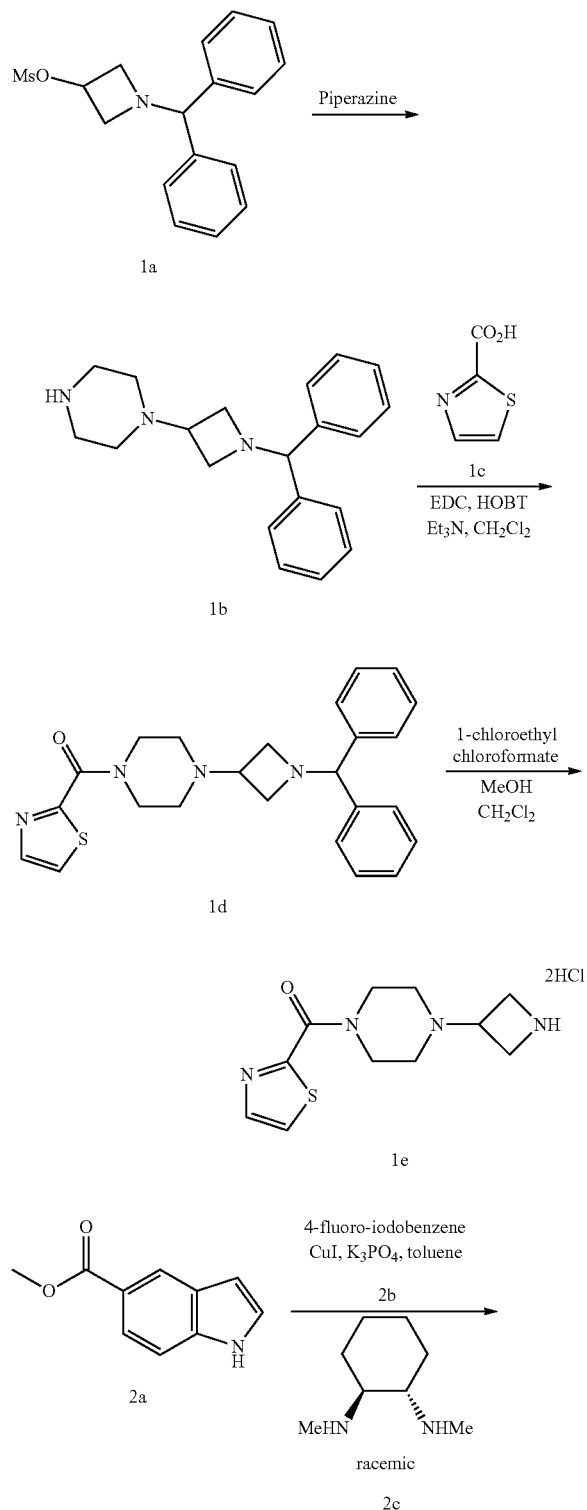

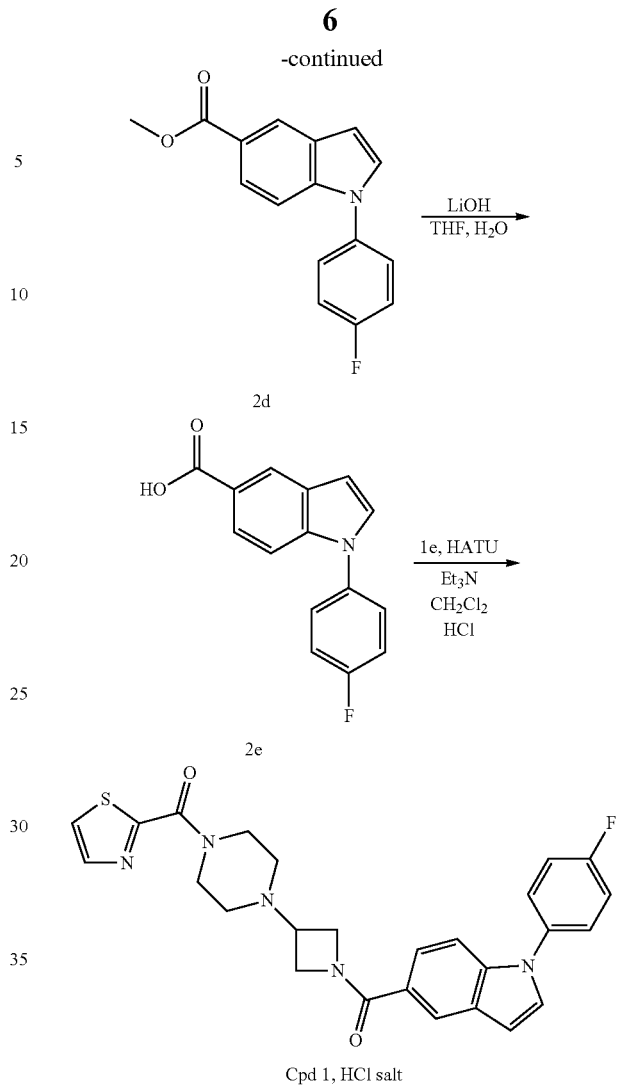

A. To a 12-L 4-neck flask equipped with mechanical stirrer, $N_2$ inlet and thermocouple was added 1-benzhydrylazetidin-3-yl methanesulfonate (1a) (250.0 g, 0.79 mol), acetonitrile (3.75 L) and piperazine (678.4 g, 7.9 mol). The reaction mixture was stirred at 80° C. for 19 h and cooled to room temperature. The reaction mixture was concentrated to half volume under reduced pressure and filtered. The white solid was washed with acetonitrile (2 L) and the filtrate was concentrated to a volume of 1 L. The filtrate was transferred to a 12-L separatory flask containing $CH_2Cl_2$ (2 L) and washed with water (1 L). The aqueous layer was back-extracted with $CH_2Cl_2$ (1 L) and the combined organic layers were washed twice with water (1 L). The organic layer was dried ($MgSO_4$), filtered, washed with $CH_2Cl_2$ (500 mL) and concentrated to dryness to give 235 g (97%) of compound 1b. $^1$H NMR (Chloroform-d) δ: 7.40 (d, J=7.3 Hz, 4H), 7.22-7.33 (m, 4H), 7.19 (d, J=7.1 Hz, 2H), 4.40 (s, 1H), 3.39 (t, J=6.5 Hz, 2H), 2.93-3.06 (m, 4H), 2.82-2.92 (m, 2H), 2.41-2.59 (m, 1H), 2.34 (br. s., 3H), 2.00 (s, 2H).

B. To a 22-L 4-neck flask equipped with mechanical stirrer, $N_2$ inlet and thermocouple was added 1-(1-benzhydrylazetidin-3-yl)piperazine (1b) (260 g, 0.85 mol), compound 1c (94.7 g, 0.65 mol), $CH_2Cl_2$ (5.2 L), HOBT (23.3 g, 0.17 mol), $Et_3N$ (0.36 L, 2.53 mol) and EDC.HCl (327.5 g, 1.7 mol). The reaction mixture was stirred for 48 h. The reaction mixture was poured into a 22-L extractor containing $CH_2Cl_2$ (4 L) and saturated NaHCO₃ (2 L). The layers were separated and the organic layer was washed with saturated NaHCO₃ (2 L) and brine (2 L). The organic layer was dried (Na₂SO₄), filtered, evaporated to dryness and the crude residue was purified by chromatography (5 Kg Biotage SiO₂ column, 15 column volumes, 4% MeOH/CH₂Cl₂) to give 317 g (90%) of compound 1d. ¹H NMR (Chloroform-d) δ: 7.85 (d, J=2.7 Hz, 1H), 7.50 (d, J=2.7 Hz, 1H), 7.34-7.46 (m, 5H), 7.23-7.32 (m, 2H), 7.14-7.22 (m, 2H), 5.27 (s, 1H), 4.42 (s, 3H), 3.81 (br. s., 2H), 3.41 (t, J=6.4 Hz, 2H), 2.96-3.06 (m, 1H), 2.89-2.95 (m, 2H), 2.37 (d, J=3.9 Hz, 4H).

C. To a 12-L 4-neck flask equipped with mechanical stirrer, N₂ inlet and thermocouple was added (4-(1-benzhydrylazetidin-3-yl)piperazin-1-yl)(thiazol-2-yl)methanone (1d) (317 g, 0.73 mol) and CH₂Cl₂ (3.07 L). The reaction mixture was cooled to 10° C. with a water/ice bath. 1-Chloroethyl chloroformate was slowly added over 5 min while maintaining the temperature at 10° C. The solution was warmed to 20° C. and stirred for 2 h. After MeOH (0.45 L) was added over 2 min, the mixture was warmed to 35° C., stirred for 2 h at 35° C., and then cooled to room temperature for 12 h. Ether (0.5 L) was added rapidly and the resulting slurry was stirred for 10 min. The white solid was collected by filtration and washed with ether (0.1 L). The white solid was dried in vacuo at 40° C. to give crude compound 1e (211 g).

The crude solid 1e (211 g) was transferred to a 5-L round bottom flask with a mechanical stirrer, N₂ inlet and thermocouple and EtOH (0.45 L) was added and the slurry was heated to 55° C. for 0.5 h. The slurry was cooled to room temperature and stirred for 1 h. The thick slurry was filtered and washed with EtOH (0.15 L). The white solid was dried in vacuo at 45° C. to give compound 1e (189 g, 79%). ¹H NMR (MeOD) δ: 7.98 (d, J=3.2 Hz, 1H), 7.89 (d, J=3.2 Hz, 1H), 4.64-4.79 (m, 2H), 4.29-4.47 (m, 4H), 3.33-3.47 (m, 3H), 3.31 (dt, 5H).

D. To a 3-L 4-neck flask equipped with mechanical stirrer, N₂ inlet and thermocouple was added compound 2a (124 g, 0.71 mol), toluene (0.99 L), 4-fluoro-iodobenzene (cpd 2b, 314.27 g, 1.42 mol), racemic trans-N,N'-dimethylcyclohexane-1,2-diamine (cpd 2c, 30.2 g, 0.21 mol), copper iodide (13.48 g, 0.078 mol) and tribasic-N-hydrate potassium phosphate (330.54 g, 1.56 mol). The mixture was heated to 85° C. for 12 h. A second charge of 4-fluoro-iodobenzene (47.14 g, 0.21 mol) was added and the mixture was heated to 85° C. for 4 h. The reaction mixture was filtered through a diatomaceous earth pad and was washed with CH₂Cl₂ (2 L). The solvent was evaporated and the residue was purified by column chromatography (2.5 Kg Biotage SiO₂ column, 15 column volumes, 10% EtOAc/Heptane) to give 110 g (58%) of compound 2d. ¹H NMR (Chloroform-d) δ: 8.45 (d, J=1.5 Hz, 1H), 7.92 (dd, J=8.8, 1.5 Hz, 1H), 7.41-7.50 (m, 3H), 7.34 (d, J=3.2 Hz, 1H), 7.17-7.29 (m, 1H), 6.77 (d, J=3.4 Hz, 1H), 3.94 (s, 3H).

E. To a 3-L 4-neck flask equipped with mechanical stirrer, N₂ inlet, condenser and thermocouple was added compound 2d (58.0 g, 0.215 mol), THF (0.58 L), deionized water (0.58 L) and lithium hydroxide (20.63 g, 0.86 mol). The reaction mixture was warmed to 55° C. for 18 h. The reaction was cooled to room temperature and the pH was adjusted to ~3 with 1M HCl (~0.8 L). A white precipitate formed during pH adjustment. The thick white slurry was filtered and washed with deionized water (0.3 L). The white solid was dried in vacuo at 45° C. to give compound 2e (53.5 g, 97%). ¹H NMR (Chloroform-d) δ: 8.54 (s, 1H), 7.99 (d, J=8.6 Hz, 1H), 7.48 (d, J=8.8 Hz, 3H), 7.36 (d, J=2.9 Hz, 1H), 7.23-7.32 (m, 2H), 6.81 (d, 1H).

F. To a 5-L 4-neck flask equipped with mechanical stirrer, N₂ inlet, condenser and thermocouple was added compound 2e (105.0 g, 0.41 mol), CH₂Cl₂ (1.58 L), Et₃N (0.344 L, 2.47 mol), (4-(azetidin-3-yl)piperazin-1-yl)(thiazol-2-yl)methanone dihydrochloride (cpd 1e, 133.8 g, 0.41 mol) and HATU (156.4 g, 0.41 mol). The reaction was stirred for 72 h at room temperature. The reaction solution was transferred to a 22-L extractor containing CH₂Cl₂ (4 L) and sat NaHCO₃ (2 L). The organic layer was washed with brine (2 L), dried (NaSO₄), filtered and evaporated to dryness. The residue was purified by column chromatography (5 Kg Biotage SiO₂ column, 3 column volumes CH₂Cl₂, 10 column volumes 3% MeOH/CH₂Cl₂) to give 189 g (94%) of compound 1 as its free base. The free base of compound 1 exhibited an onset melting temperature of about 158.09° C. and a peak temperature of melting of about 187.15° C. ¹H NMR (MeOD) δ: 7.99 (s, 1H), 7.93 (d, J=3.4 Hz, 1H), 7.81 (d, J=3.2 Hz, 1H), 7.44-7.62 (m, 5H), 7.23-7.39 (m, 2H), 6.77 (d, J=3.4 Hz, 1H), 4.43-4.53 (m, 1H), 4.39 (br. s., 1H), 4.17-4.34 (m, 2H), 4.06 (dd, J=10.0, 4.9 Hz, 1H), 3.80 (br. s., 1H), 3.28-3.38 (m, 2H), 3.18-3.28 (m, 1H), 2.50 (br. s., 4H).

To a 5-L 4-neck flask equipped with mechanical stirrer, N₂ inlet, condenser and thermocouple was added crude compound 1 free base (147.6 g, 0.301 mol) and dichloromethane (0.738 L). 1.0 M HCl (0.301 L) was added over 5 min. After 1 h, Et₂O (1.476 L) was added over 5 min. The white slurry was filtered, washed with Et₂O (0.1 L) and dried in vacuo at 45° C. to give compound 1 (139 g, 88%) as its hydrochloride salt. The hydrochloride salt of compound 1 exhibited an onset melting temperature of about 164.24° C. and a peak temperature of melting of about 193.33° C.

Preparation of Crystalline Hydrochloride Salt of Compound 1

To a 5-L 4-neck flask equipped with a mechanical stirrer, N₂ inlet, condenser and thermocouple was added the hydrochloride salt of compound 1 (139 g, 0.264 mol) and a 1:1 mixture of MeOH and EtOH (1.112 L). The slurry was stirred at 70° C. for 3 h and allowed to cool to room temperature. The flask was placed in an ice bath for 2 h and the white slurry was filtered in a medium sintered glass funnel and washed with a 1:1 EtOH and MeOH (100 mL) solution. The cake was placed in a vacuum oven at 50° C. for 2 days. The material was collected to give 127 g (91.3%) of the Form a crystal of compound 1. ¹H NMR (DMSO-d₆) δ: 12.57-12.97 (m, 1H), 8.11 (d, J=3.2 Hz, 1H), 8.06 (d, J=3.2 Hz, 1H), 8.01 (s, 1H), 7.76 (d, J=3.2 Hz, 1H), 7.61-7.70 (m, 2H), 7.50-7.57 (m, 2H), 7.45 (t, J=8.7 Hz, 2H), 6.82 (d, J=3.2 Hz, 1H), 5.63 (br. s., 1H), 4.38-4.87 (m, 4H), 4.05-4.37 (m, 3H), 3.51-3.95 (m, 4H), 2.93-3.28 (m, 2H);

Elemental Analysis
$C_{26}H_{24}F_1N_5O_2S \cdot 1.06HCl \cdot 0.04H_2O \cdot 0.45C_2H_6O_1$,
Theory: % C=59.07; % H=5.11; % N=13.14; % F=3.47; % S=5.86; % Cl=6.48;
Found: % C=58.87; % H=4.77; % N=12.80; % F=3.77; % S=5.92; % Cl=6.53.
% H₂O found=<0.1.

% Ash=<0.1.

Powder X-Ray Diffraction (pXRD)

The crystalline form of the hydrochloride salt of compound 1 was characterized by its powder X-ray diffraction pattern (pXRD) as follows. The sample was examined using an X-ray diffractometer (Philips Model X'PERT PRO MPD) with X'Celerator detector and graded multilayer parabolic X-ray mirror. The samples were scanned from 3 to 35°2θ, at a step size 0.0165°2θ and a time per step of 10.16 seconds. The effective scan speed is 0.2067°/s. The tube voltage and current were 45 KV and 40 mA, respectively. The sample was packed on a zero background XRD-holder and scanned under ambient temperature and humidity conditions.

A pXRD spectrum was measured for a representative sample of the crystalline form of the hydrochloride salt of compound 1, as shown in FIG. 1. In an embodiment, the crystalline form of the hydrochloride salt of compound 1 may be characterized by its powder X-ray diffraction pattern, which includes the peaks listed in Table 1, below.

TABLE 1 pXRD Peaks: Crystalline Form of the Hydrochloride Salt of Cpd 1

| Pos. [°2Th.] | d-spacing [Å] | Rel. Int. [%] |
|---|---|---|
| 4.68 | 18.89616 | 100 |
| 8.80 | 10.04547 | 71.78 |
| 9.29 | 9.52416 | 93.14 |
| 9.63 | 9.18692 | 33.82 |
| 11.89 | 7.44156 | 14.26 |
| 14.96 | 5.92296 | 23.03 |
| 16.66 | 5.32017 | 48.46 |
| 17.50 | 5.06835 | 61.28 |
| 18.09 | 4.90414 | 41.94 |
| 18.57 | 4.77799 | 50.4 |
| 19.27 | 4.60501 | 57.62 |
| 20.41 | 4.35121 | 26.88 |
| 21.45 | 4.14348 | 34.21 |
| 23.08 | 3.85291 | 52.41 |
| 23.88 | 3.72579 | 35.69 |
| 25.72 | 3.46338 | 25.62 |
| 26.47 | 3.3677 | 29.11 |

In an embodiment, the crystalline form of the hydrochloride salt of compound 1 is characterized by its pXRD pattern that includes peaks having a relative intensity greater than or equal to about 30%, as listed in Table 2, below.

TABLE 2 pXRD Peaks: Crystalline Form of the Hydrochloride Salt of Cpd 1

| Pos. [°2Th.] | d-spacing [Å] | Rel. Int. [%] |
|---|---|---|
| 4.68 | 18.89616 | 100 |
| 8.80 | 10.04547 | 71.78 |
| 9.29 | 9.52416 | 93.14 |
| 9.63 | 9.18692 | 33.82 |
| 16.66 | 5.32017 | 48.46 |
| 17.50 | 5.06835 | 61.28 |
| 18.09 | 4.90414 | 41.94 |
| 18.57 | 4.77799 | 50.4 |
| 19.27 | 4.60501 | 57.62 |
| 21.45 | 4.14348 | 34.21 |
| 23.08 | 3.85291 | 52.41 |
| 23.88 | 3.72579 | 35.69 |

In an embodiment, the crystalline form of the hydrochloride salt of compound 1 is characterized by its pXRD pattern that includes peaks having a relative intensity greater than or equal to about 40%, as listed in Table 3, below.

TABLE 3 pXRD Peaks: Crystalline Form of the Hydrochloride Salt of Cpd 1

| Pos. [°2Th.] | d-spacing [Å] | Rel. Int. [%] |
|---|---|---|
| 4.68 | 18.89616 | 100 |
| 8.80 | 10.04547 | 71.78 |
| 9.29 | 9.52416 | 93.14 |
| 16.66 | 5.32017 | 48.46 |
| 17.50 | 5.06835 | 61.28 |
| 18.09 | 4.90414 | 41.94 |
| 18.57 | 4.77799 | 50.4 |
| 19.27 | 4.60501 | 57.62 |
| 23.08 | 3.85291 | 52.41 |

In an embodiment, the crystalline form of the hydrochloride salt of compound 1 is characterized by its pXRD pattern that includes peaks having a relative intensity greater than or equal to about 50%, as listed in Table 4, below.

TABLE 4 pXRD Peaks: Crystalline Form of the Hydrochloride Salt of Cpd 1

| Pos. [°2Th.] | d-spacing [Å] | Rel. Int. [%] |
|---|---|---|
| 4.68 | 18.89616 | 100 |
| 8.80 | 10.04547 | 71.78 |
| 9.29 | 9.52416 | 93.14 |
| 17.50 | 5.06835 | 61.28 |
| 18.57 | 4.77799 | 50.4 |
| 19.27 | 4.60501 | 57.62 |
| 23.08 | 3.85291 | 52.41 |

In another embodiment, the present invention is directed to a crystalline form of the hydrochloride salt of compound 1 as characterized by the following pXRD peaks, listed in °2θ: 4.68, 8.80, 9.29, 16.66, 17.50, 18.57, and 19.27. In another embodiment, the present invention is directed to a crystalline form of the hydrochloride salt of compound 1 as characterized by the following pXRD peaks, listed in °2θ: 4.68, 9.29, 16.66, and 17.50.

Differential Scanning Calorimetry (DSC)

The crystalline form of the hydrochloride salt of compound 1 was further subjected to DSC analysis. A representative sample was tested using a TA Instruments Model Q100 differential scanning calorimeter. The sample was analyzed as received in an open aluminum pan. The DSC was programmed to heat from 25° C. to 350° C. at a heating rate of 10° C./min with an air purge.

Figure 2:
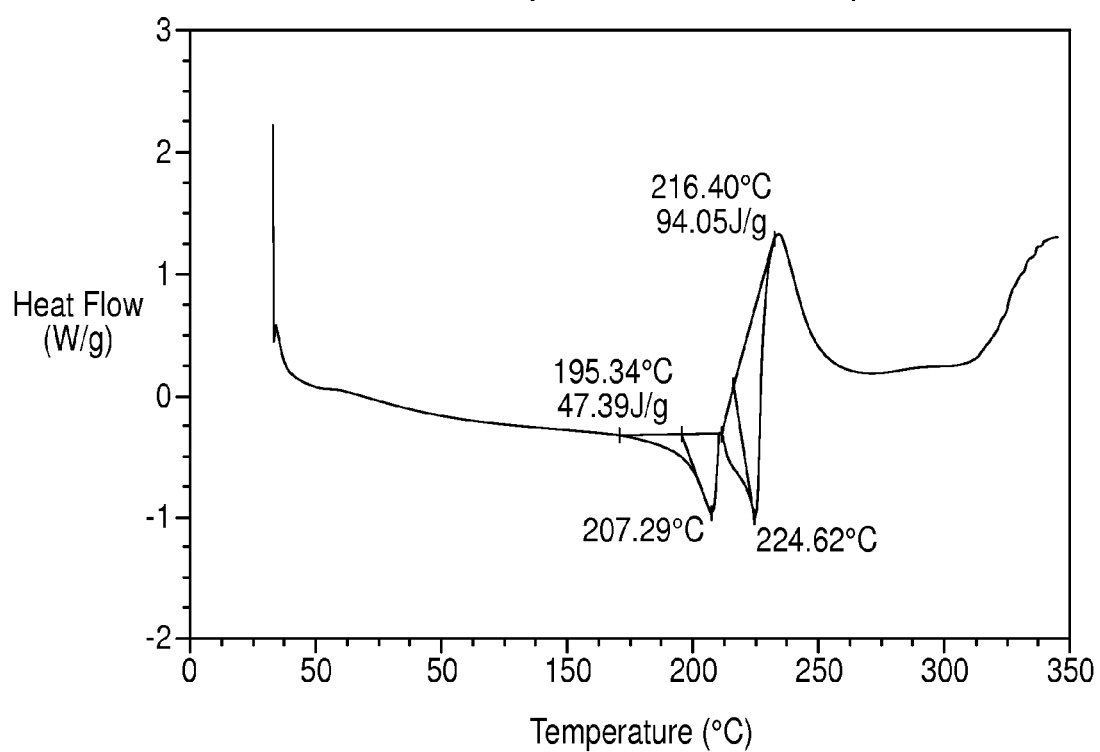
FIG. 2 illustrates a representative differential scanning calorimetry (DSC) scan for the crystalline hydrochloride salt of compound 1.

Thermal analysis (via DSC scanning) was completed for a representative sample of the crystalline form of the hydrochloride salt of compound 1, as shown in FIG. 2. The crystalline hydrochloride salt of compound 1 exhibited an onset melting temperature of about 195.34° C., a peak temperature of melting of about 207.29° C. and an enthalpy of 47.39 J/g.

Thermogravimetric Analysis (TGA)

The crystalline hydrochloride salt of compound 1 was further subjected to TGA analysis. A representative sample was tested, as received, for total weight loss using a Mettler Toledo SDTA851 thermogravimetric calorimeter. The sample was placed in a 70 μL alumina pan, automatically weighed and inserted into the TGA furnace. The sample was scanned from 35° C. to 350° C. at a heating rate of 10° C./min.

Figure 3:
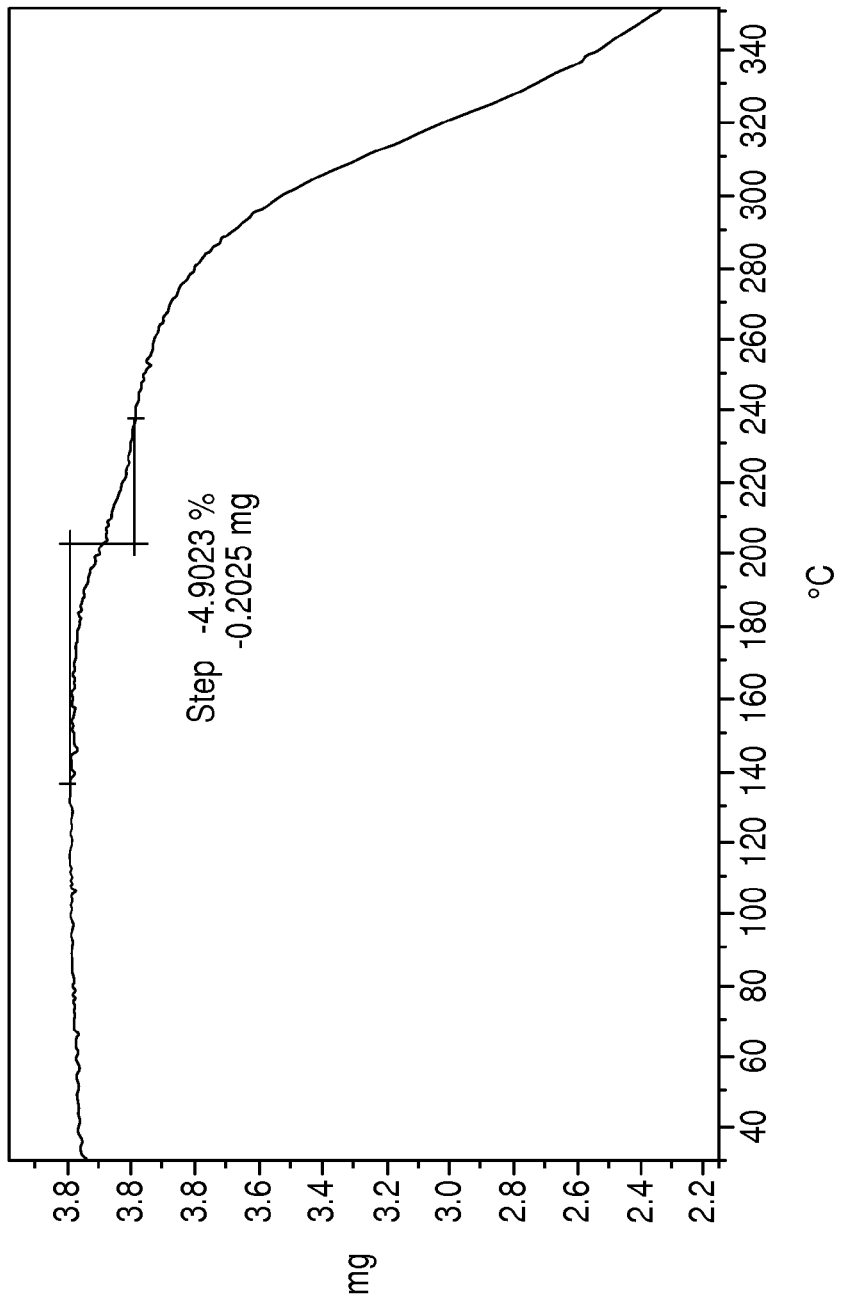
FIG. 3 illustrates a representative thermal gravimetric analysis (TGA) scan for the crystalline hydrochloride salt of compound 1.

A TGA trace was measured for a representative sample of the crystalline form of the hydrochloride salt of compound 1, as shown in FIG. 3.

The crystalline hydrochloride salt of (1-(4-fluorophenyl)-1H-indol-5-yl)(3-(4-(thiazole-2-carbonyl)piperazin-1-yl)azetidin-1-yl)methanone of the present invention can be characterized by the TGA or DSC data, or by any one, any two, any three, any four, any five, any six, any seven, any eight, any nine, or any ten PXRD 2-theta angle peaks, or by any combination of the data acquired from the analytical techniques described above which distinctly identify the particular crystal.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A crystalline hydrochloride salt of compound 1

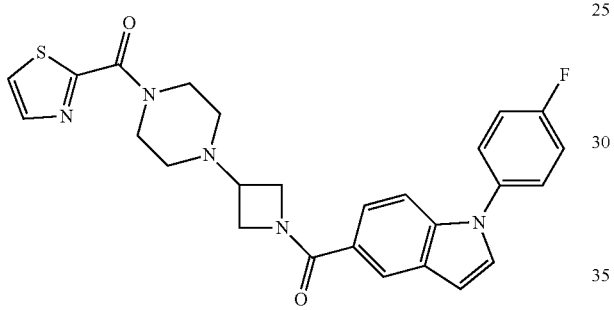

Cpd 1 comprising powder X-ray diffraction peaks of about 4.68, about 9.29, about 16.66, and about 17.50 °2θ.

2. A crystalline hydrochloride salt of compound 1

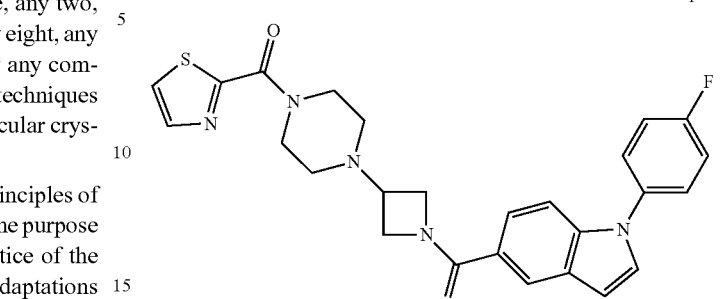

Cpd 1 comprising powder X-ray diffraction peaks, listed in °2θ, of: 4.68, 8.80, 9.29, 16.66, 17.50, 18.09, 18.57, 19.27, and 23.08.

3. A crystalline hydrochloride salt of compound 1

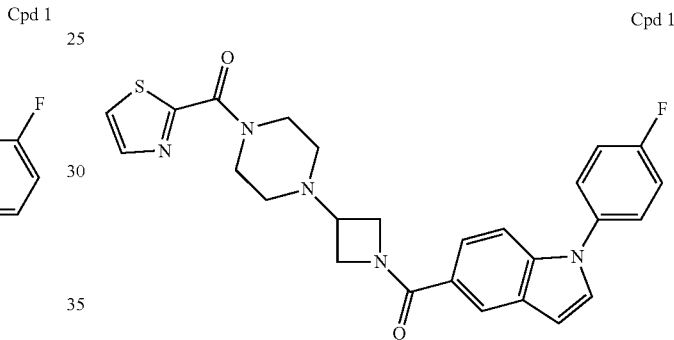

Cpd 1 comprising powder X-ray diffraction peaks, listed in °2θ, of: 4.68, 8.80, 9.29, 17.50, 18.57, 19.27, and 23.08.

* * * * *